United States Patent [19]

Ehr

[11] 4,455,313

[45] Jun. 19, 1984

[54] FUNGICIDAL CONTROL EMPLOYING SUBSTITUTED PYRIDINOLS

[75] Inventor: Robert J. Ehr, Pittsburg, Calif.

[73] Assignee: The Dow Chemical Company, Midland, Mich.

[21] Appl. No.: 409,793

[22] Filed: Aug. 20, 1982

[51] Int. Cl.$^3$ .................. A01N 43/40; A01N 55/02
[52] U.S. Cl. ................................. 424/263; 424/245
[58] Field of Search .......................... 424/263, 245

[56] References Cited

U.S. PATENT DOCUMENTS

| | | | |
|---|---|---|---|
| 3,244,722 | 5/1966 | Johnston et al. | 424/263 |
| 3,249,419 | 5/1966 | Martin | 71/2.5 |
| 3,609,158 | 9/1971 | Torba | 424/263 |
| 3,682,938 | 8/1972 | Troxel et al. | 424/263 |
| 3,705,170 | 12/1972 | Torba | 424/263 |
| 3,706,751 | 12/1972 | Domenico | 424/263 |
| 3,711,486 | 1/1973 | Torba | 424/263 |
| 3,891,760 | 6/1975 | O'Melia | 424/263 |
| 4,062,962 | 12/1977 | Noveroske | 424/263 |
| 4,143,144 | 3/1979 | Tobol et al. | 424/263 |
| 4,190,662 | 2/1980 | Fenstermacher et al. | 424/263 |

*Primary Examiner*—Douglas W. Robinson
*Attorney, Agent, or Firm*—S. Preston Jones; Ronald G. Brookens

[57] ABSTRACT

Crop plants are protected from attack by soil-borne plant disease organisms of the Genera Rhizoctonia and Sclerotium employing 2-halo-4-halomethyl 6-pyridinols and their metal and amine salts.

14 Claims, No Drawings

FUNGICIDAL CONTROL EMPLOYING SUBSTITUTED PYRIDINOLS

SUMMARY OF THE INVENTION

The present invention is directed to a method for protecting plants planted in soil containing soil-borne plant disease organisms of the Genera Rhizoctonia and Sclerotium employing as the active materials substituted pyridinols and their derivatives which correspond to the formula

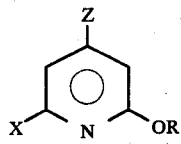

(Formula I)

wherein

X represents bromo, chloro, fluoro or iodo;

Z represents trichloromethyl, trifluoromethyl, dichloromethyl, dichlorofluoromethyl or chlorodifluoromethyl and R represents hydrogen, alkali metal, alkaline earth metal, zinc, iron, aluminum, copper, manganese or $-NR^1R^2R^3$ wherein $R^1$, $R^2$ and $R^3$ are each independently hydrogen or alkyl of 1 to 4 carbon atoms.

In the present specification and claims, the term "alkali metal" is employed to designate sodium, potassium, lithium and cesium; the term "alkaline earth metal" is employed to designate calcium, barium or strontium; and the term "alkyl" is employed to designate straight and branched chain alkyl groups of from 1 to 4 carbon atoms.

In the present specification and claims, the term "systemic" defines the translocation of the active compounds employed in the present method through the plant. The active compounds can be applied either to the above-ground or preferably to below-ground portions of the plant.

In the present specification and claims, the term "plant part" is employed to designate all parts of a plant and includes seeds, bulbs, stolons, tubers, rhizomes, ratoons, corms, the root system hereinafter commonly referred to as root, the crown, stalk, stem, foliage or leaf system fruit or flower.

Examples of compounds which are active agents in the present method include:

2-(Bromo-, chloro-, fluoro- or iodo)-4-(trichloromethyl)-6-pyridinol;
2-(Bromo-, chloro-, fluoro- or iodo-)-4-(dichloromethyl)-6-pyridinol;
2-(Bromo-, chloro-, fluoro- or iodo-)-4-(dichlorofluoromethyl)-6-pyridinol;
2-(Bromo-, chloro-, fluoro- or iodo-)-4-(dichloromethyl)-6-pyridinol, ammonium salt;
2-(Bromo-, chloro-, fluoro- or iodo-)-4-(trichloromethyl)-6-pyridinol, sodium salt;
2-(Bromo-, chloro-, fluoro- or iodo-)-4-(trichloromethyl)-6-pyridinol, potassium salt;
2-(Bromo-, chloro-, fluoro- or iodo-)-4-(trichloromethyl)-6-pyridinol, zinc salt;
2-(Bromo-, chloro-, fluoro- or iodo-)-4-(trichloromethyl)-6-pyridinol, copper salt;
2-(Bromo-, chloro-, fluoro- or iodo-)-4-(dichloromethyl)-6-pyridinol, aluminum salt;
2-(Bromo-, chloro-, fluoro- or iodo-)-4-(dichlorofluoromethyl)-6-pyridinol, iron salt;
2-(Bromo-, chloro-, fluoro- or iodo-)-4-(dichlorofluoromethyl)-6-pyridinol, lithium salt;
2-(Bromo-, chloro-, fluoro- or iodo-)-4-(dichloromethyl)-6-pyridinol, calcium salt;
2-(Bromo-, chloro-, fluoro- or iodo-)-4-(dichloromethyl)-6-pyridinol, cesium salt;
2-(Bromo-, chloro-, fluoro- or iodo-)-4-(dichlorofluoromethyl)-6-pyridinol, barium salt;
2-(Bromo-, chloro-, fluoro- or iodo-)-4-(dichlorofluoromethyl)-6-pyridinol, strontium salt;
2-(Bromo-, chloro-, fluoro- or iodo-)-4-(chlorodifluoromethyl)-6-pyridinol, methylamine salt;
2-(Bromo-, chloro-, fluoro- or iodo-)-4-(trifluoromethyl)-6-pyridinol, dimethylamine salt;
2-(Bromo-, chloro-, fluoro- or iodo-)-4-(trifluoromethyl)-6-pyridinol, butylamine salt; and
2-(Bromo-, chloro-, fluoro- or iodo-)-4-(chloromethyl)-6-pyridinol, dibutylamine salt.

Preferred compounds for use in the present method are those compounds of Formula I wherein Z is trichloromethyl; more preferred compounds are those wherein Z is trichloromethyl and X is chloro and the most preferred compounds are those wherein Z is trichloromethyl, X is chloro and R is hydrogen or an alkali metal.

Compositions containing one or more of the active compounds of the present invention have been found to be very effective in the control of the plant diseases caused by Rhizoctonia and/or Sclerotium either before or after the plant has been attacked by said disease organisms.

Control of soil-borne plant disease by the present invention is achieved, for example, in cereal crops such as corn, wheat, barley, rye, oats, rice and sorghum; vegetable crops such as tomatoes, peppers, lettuce, onions, cabbage, broccoli, squash, cucumber, cauliflower, etc., legumes such as peanuts, soybeans, peas and alfalfa; root crops such as turnips, beets, carrots, white potatoes, sweet potatoes and yams; fiber crops such as cotton, flax and hemp; fruit crops such as apples, bananas, cantaloupes, cherries, dates, figs, grapes, pineapples, grapefruit, lemons, limes, oranges, peaches, pears, plums, strawberries and watermelon; oil crops such as castorbean, copra, olives, palms, rubber and sunflower; stimulants such as cocoa, coffee, tea and tobacco; sugar crops such as sugar cane and sugar beets; turf including bent grass and blue grass, rye and fescue; ornamentals such as chrysanthemums, zinnias, carnations, lilies, violets, petunias, marigolds, philodendrons, schefflera, dracaena, wax plants, jade plant, ivy, ferns, rubber plants, cactus and dieffenbachia; woody ornamentals such as pines, roses, rhododendron, azaleas, boxwood, spruce and the like. While the above lists a variety of crop plants which may be treated by the practice of the present invention, it is to be understood that the present method is not restricted to the above list of crop plants.

Generally in the actual practice of the method of the present invention, a non-phytotoxic plant protecting amount of the active toxicant compounds can be applied to the plant or plant part by a variety of convenient procedures. Such procedures include soil incorporation whereby compositions containing the active toxicant are mechanically mixed with the soil; applied to the surface of the soil and thereafter dragged, disced or rototilled into the soil; or transported into the soil with a liquid carrier such as by injection, spraying or irrigation. Additionally, a plant protecting amount of the active toxicant compounds can be employed in sprays, gels or coatings for above-ground applications or drenched onto the soil surface. In additional application methods, the active toxicant can be applied by vapor transfer; added in liquid or solid composition to hydroponic operations; seed treatment operations and by conventional plant part coating operations or other techniques known to those skilled in the art. The only limitation upon the mode of application employed is that it must be one which will allow the toxicant to come in contact with plants or plant parts.

The exact dosage of the active toxicant employed can be varied depending upon the specific plant, its stage of development, hardiness, the mode of application and its growth media. Generally, the active ingredient should be present in an amount equivalent to from about 50 micrograms to about 140 grams or more per plant on a per plant basis. Translating this into conventional application rates, this amount is equivalent to from about 0.0005 pound to about 10 pounds or more of the active ingredient on a per acre basis, as chemical available to the plant.

It will be appreciated that on a per plant basis, seed treatment of small seeded plant species such as grasses, carrots and the like will actually require much smaller amounts than 50 micrograms per plant. Generally, rates in the range of 1/32 to about 8 ounces per 100 pounds of seeds will be optimum for seed treatment among the diversity of plant species. For practices such as conventional tobacco transplant treatment or in-furrow soil treatment of plants such as soybeans at seeding and the like, an amount of active toxicant approximately equal to 8 to about 32 milligrams would be utilized on a per plant basis.

Larger amounts of the active ingredient may advantageously be applied when treatments are employed which distribute the material throughout the soil. For example, when the active ingredient is applied as an atplant row treatment or as an early or mid-season post-plant side dress treatment, those amounts of chemical not proximal to plant roots are essentially unavailable to the plant and therefore not effective as set forth hereinabove. In such practices, the amount of the active ingredient employed needs to be increased to rates as high as about 20 pounds per acre or higher to assure that the requisite effective quantity of active ingredient is made available to the plants.

The present invention can be carried out by employing the pyridinol compounds directly, either singly or in combination. However, the present invention also embraces the employment of liquids, dusts, waxes, gels, jellies, wettable powders, granules or encapsulated compositions containing at least one of said compounds as active ingredient. In such usage, the compound or compounds can be modified with one or more of a plurality of additaments or soil-modifying adjuvants including fertilizers, nematicides, herbicides, insecticides or other pesticidal adjuvants or inert solvents, inert liquid carriers and/or surface active dispersing agents and coarsely or finely divided inert solids. The augumented compositions are also adapted to be employed as concentrates and subsequently diluted with additional inert carrier to produce other compositions in the form of dusts, sprays, granules, washes or drenches. In compositions where the adjuvant is a coarsely or finely divided solid, a surface active agent or the combination of a surface active agent and a liquid additament, the adjuvant cooperates with the active component so as to facilitate the invention. Whether the composition is employed in liquid, wettable powder, gel, wax, jelly, dust granule or encapsulated form, the active compound will normally be present in an amount of from about 2 to 98 percent by weight of the total composition.

In the preparation of dust, wettable powders or other solid compositions, the toxicant products can be compounded with any of the finely divided solids, such as pyrophyllite, talc, chalk, gypsum, fullers's earth, bentonite, attapulgite, modified clays, starch, casein, gluten and the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular fomulations are usually prepared by impregnating a solution of the toxicant in a volatile organic solvent onto a bed of coarsely divided attapulgite, bentonite, diatomite or the like.

Additionally, gels containing the desired amount of one of the active compounds can be prepared by dispersing the active compound in an inert aqueous or organic based liquid and thereafter treating said mixture with a gelling medium such as crosslinked alkaline salts of polyacrylic acid, methyl cellulose, carboxymethyl cellulose, tertiary butyl styrene, modified clays or other conventional gelling mediums.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable inert organic liquids which can be employed in the compositions include vegetable oils or petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other compositions containing the desired amount of effective agent can be prepared by dispersing the toxicant in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° C. The proportion of the compounds of this invention employed in a suitable solvent may vary from about 2 to about 50 percent or higher. Additionally, the active components can be compounded with waxes or petroleum jellies to prepare viscous or semi-solid treating compositions.

A preferred liquid composition includes the use of the active compound or compounds in combination with surface-active dispersant agents only. In such compositions, it is preferred to use ionic and non-ionic blends of such dispersant agents in combination with one or more of the active materials. A particular advantage of such a formulation is that phytotoxicity associated with certain inert solvents, such as, xylene, methylene chloride and like materials can be avoided. Generally, the use of such formulations will result in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench treatments and the like.

Water miscible organic solvents such as lower alcohols or propylene glycol can be added to depress the freezing point and further cooperate with the above system in that they are essentially non-phytotoxic.

The expression "soil" is employed herein in its broadest sense to be inclusive of all conventional soils, as defined in Webster's New International Dictionary, Second Edition, Unabridged, published in 1937, G. C. Merriam Co, Springfield, Mass. Thus, the term refers to any substance or medium in which plants may take root and grow and is intended to include not only earth, but also compost, manure, muck, sand, synthetic growth mediums such as vermiculite and pearlite and the like, adapted to support plant growth.

DESCRIPTION OF THE PREFERRED EMBODIMENTS

In order that the present invention may be more fully understood, the following examples are given to illustrate the manner by which it can be practiced but, as such, should not be construed as limitations upon the overall scope of the same.

EXAMPLE I

Acetone dispersions were prepared by admixing predetermined amounts of one of the active compounds with predetermined amounts of acetone.

Soil infected with the causative disease organism of root rot and seeding damping off, i.e., *Rhizoctonia solani* was uniformly mixed and placed in 3-inch pots. Cotton seeds of the variety "Acala SJ-2" were uniformly treated with predetermined amounts of the above acetone dispersions. Ten seeds were planted in each pot. Additional seeds which had been treated with acetone alone were also planted to serve as controls. After planting, the pots containing the seeds were maintained under greenhouse conditions conducive to both plant growth and disease development. About one week after treatment, the pots were examined to determine the minimum concentration of the active compound necessary to give at least a 90 percent kill and control of the above indicated disease organism. The results of this examination are set forth below in Table I.

TABLE I

| Compound employed | Minimum concentration of compound in part of active compound per million parts of the ultimate composition (ppm) to give at least 90 percent kill and control of *Rhizoctonia solani* |
|---|---|
| 2-Fluoro-4-trichloromethyl-6-pyridinol | 6 |
| 2-Chloro-4-trichloromethyl-6-pyridinol | 15 |
| 2-Bromo-4-trichloromethyl-6-pyridinol | 5 |

EXAMPLE II

Acetone dispersions were prepared by admixing predetermined amounts of 2-chloro-4-trichloromethyl-6-pyridinol with predetermined amounts of acetone.

The dispersions were dispersed in varying amounts of warm melted nutrient agar to prepare culture media containing one of the active compounds in predetermined concentrations. The melted agar dispersions were poured into petri dishes and allowed to solidify. The solidified surface in each dish was inoculated with a culture of *Rhizoctonia solani*. In another operation, petri dishes containing toxicant free nutrient agar are inoculated in the same manner to serve as controls. The dishes were thereafter incubated for 3 days after which they were examined and it was determined that at 15 ppm the compound tested gave 90 percent kill and control of *Rhizoctonia solani* in the nutrient agar. At the time of the examination, the control dishes were found to support a heavy growth of the above named organism.

EXAMPLE III

Acetone dispersions were prepared by admixing predetermined amounts of one of the active compounds with predetermined amounts of acetone.

Soil infected with the causative disease organism of root rot and seeding damping off, i.e., *Rhizoctonia solani* was uniformly mixed and placed in 3-inch pots. Cotton seeds of the variety "Acala SJ-2" were uniformly treated with an amount of the above acetone dispersions equivalent to treating 100 pounds of seeds with eight ounces of the active compound. Ten seeds were planted in each pot. Additional seeds which had been treated with acetone alone were also planted to serve as controls. After planting, the pots containing the seeds were maintained under greenhouse conditions conducive to both plant growth and disease development. About eighteen days after treatment, the pots were examined to determine the percent of the cotton plants surviving. The results of this examination are set forth below in Table II.

TABLE II

| Compound employed | Percent of cotton plants surviving after growing 18 days in soil infected with *Rhizoctonia solani* |
|---|---|
| 2-Fluoro-4-trichloromethyl-6-pyridinol | 80 |
| 2-Chloro-4-trichloromethyl-6-pyridinol | 100 |
| 2-Bromo-4-trichloromethyl- | 100 |

TABLE II-continued

| Compound employed | Percent of cotton plants surviving after growing 18 days in soil infected with *Rhizoctonia solani* |
| --- | --- |
| 6-pyridinol | |

EXAMPLE IV

Acetone dispersions were prepared by admixing predetermined amounts of one of the active compounds with predetermined amounts of acetone.

The dispersions were dispersed in varying amounts of warm melted nutrient agar to prepare culture media containing one of the active compounds in predetermined concentrations. The melted agar dispersions were poured into petri dishes and allowed to solidify. The solidified surface in each dish was inoculated with a culture of *Sclerotium rolfsii*. In another operation, petri dishes containing toxicant free nutrient agar are inoculated in the same manner to serve as controls. The dishes were thereafter incubated for 5 days after which they were examined to determine the minimum concentration of each compound tested to give 90 percent kill and control of *Sclerotium rolfsii* in the nutrient agar. At the time of the examination, the control dishes were found to support a heavy growth of the above named organism. The results of this examination are set forth below in Table III.

TABLE III

| Compound employed | Minimum concentration of compound in ppm to give at least 90 percent kill and control of *Sclerotium rolfsii* |
| --- | --- |
| 2-Chloro-4-dichloromethyl-6-pyridinol | 50 |
| 2-Chloro-4-trichloromethyl-6-pyridinol | 45 |
| 2-Chloro-4-trifluoromethyl-6-pyridinol | 17 |

The substituted pyridinols employed as the active compounds in the presently claimed method are for the most part known compounds.

The compounds wherein R is hydrogen (OR is hydroxy) can be prepared by refluxing an appropriate 4-halomethyl-2-halo-6-alkoxypyridine with a moderately concentrated mineral acid such as HCl for about ½ to 4 hours.

The metal and amine salts of the above 4-halomethyl-2-halo-6-hydroxy pyridines can be prepared by mixing equimolar or equivalent proportions of an appropriate hydroxy pyridine and an hydroxide of an appropriate metal or amine, preferably in the presence of a solvent or dispersion medium and thereafter evaporating off all water. Other conventional procedures for preparing salts can also be employed.

What is claimed is:

1. A method for protecting plants planted in soil containing soil-borne plant disease organisms of the Genera *Rhizoctonia* and *Sclerotium* from attack by said soil-borne plant disease organisms which comprises contacting plants or plant parts with a non-phytotoxic plant protecting amount of a plant protectant of the formula

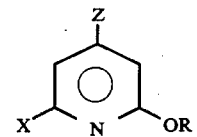

wherein
   X represents bromo, chloro, fluoro or iodo;
   Z represents trichloromethyl, trifluoromethyl, dichloromethyl, dichlorofluoromethyl or chlorodifluoromethyl and
   R represents hydrogen, alkali metal, alkaline earth metal, zinc, iron, aluminum, copper, manganese or $-NR^1R^2R^3$ wherein $R^1$, $R^2$ and $R^3$ are each independently hydrogen or alkyl of 1 to 4 carbon atoms, in intimate admixture with an inert adjuvant therefor.

2. The method as defined in claim 1 wherein the plant protector is 2-chloro-4-dichloromethyl 6-pyridinol.

3. The method as defined in claim 1 wherein the plant protector is 2-chloro-4-trichloromethyl 6-pyridinol.

4. The method as defined in claim 1 wherein the plant protector is 2-chloro-4-trifluoromethyl 6-pyridinol.

5. The method as defined in claim 1 wherein the plant protector is 2-bromo-4-trichloromethyl 6-pyridinol.

6. The method as defined in claim 1 wherein the plant protector is 2-bromo-4-trifluoromethyl 6-pyridinol.

7. The method as defined in claim 1 wherein the plant protector is 2-fluoro-4-trichloromethyl 6-pyridinol.

8. The method as defined in claim 1 wherein plant seeds are treated with the plant protector.

9. The method as defined in claim 8 wherein the plant protector is 2-chloro-4-dichloromethyl 6-pyridinol.

10. The method as defined in claim 8 wherein the plant protector is 2-chloro-4-trichloromethyl 6-pyridinol.

11. The method as defined in claim 8 wherein the plant protector is 2-chloro-4-trifluoromethyl 6-pyridinol.

12. The method as defined in claim 8 wherein the plant protector is 2-bromo-4-trichloromethyl 6-pyridinol.

13. The method as defined in claim 8 wherein the plant protector is 2-bromo-4-trifluoromethyl 6-pyridinol.

14. The method as defined in claim 8 wherein the plant protector is 2-fluoro-4-trichloromethyl 6-pyridinol.

* * * * *